United States Patent
Manukyan et al.

(10) Patent No.: US 12,402,992 B2
(45) Date of Patent: Sep. 2, 2025

(54) METHOD FOR INSTALLING CERAMIC VENEERS WITHOUT TOOTH-GRINDING

(71) Applicants: Artavazd Genrikovich Manukyan, Dubai (AE); Genrik Manukian, Dubai (AE)

(72) Inventors: Artavazd Genrikovich Manukyan, Dubai (AE); Genrik Manukian, Dubai (AE)

(*) Notice: Subject to any disclaimer, the term of this patent is extended or adjusted under 35 U.S.C. 154(b) by 0 days.

(21) Appl. No.: 19/018,017

(22) Filed: Jan. 13, 2025

(65) Prior Publication Data
US 2025/0143851 A1 May 8, 2025

Related U.S. Application Data

(63) Continuation-in-part of application No. 17/617,933, filed as application No. PCT/RU2021/000049 on Feb. 5, 2021, now abandoned.

(51) Int. Cl.
| A61C 13/083 | (2006.01) |
| A61C 3/025 | (2006.01) |
| A61C 13/15 | (2006.01) |
| A61K 6/30 | (2020.01) |

(52) U.S. Cl.
CPC ............ A61C 13/083 (2013.01); A61C 3/025 (2013.01); A61C 19/003 (2013.01); A61K 6/30 (2020.01)

(58) Field of Classification Search
CPC .................................... A61C 5/20; A61C 5/30
See application file for complete search history.

(56) References Cited

U.S. PATENT DOCUMENTS

| 4,934,936 A * | 6/1990 | Miller ................... A61C 13/30 433/221 |
| 5,008,304 A * | 4/1991 | Kmentt .................. C08K 9/06 523/213 |
| 5,183,397 A * | 2/1993 | Weissman ................ A61C 5/30 433/226 |
| 5,267,855 A * | 12/1993 | Tuneberg ................. A61C 7/16 433/9 |
| 5,575,649 A * | 11/1996 | Lee ......................... A61C 3/00 433/141 |
| 9,877,800 B1 * | 1/2018 | Silverman ............ A61C 19/066 |
| 2005/0227204 A1 * | 10/2005 | Hauck ...................... A61C 5/20 433/218 |
| 2007/0292821 A1 * | 12/2007 | De Vreese ............ A61C 13/08 433/195 |
| 2008/0014559 A1 * | 1/2008 | Love ........................ A61C 5/20 433/29 |
| 2013/0115573 A1 * | 5/2013 | Lampl ..................... A61K 6/30 433/219 |
| 2019/0350677 A1 * | 11/2019 | Sorenson ................ A61K 6/17 |
| 2022/0008180 A1 * | 1/2022 | Van Der Poel ...... A61C 19/043 |
| 2022/0313390 A1 * | 10/2022 | Manukyan ............... A61C 5/20 |

FOREIGN PATENT DOCUMENTS

| CN | 116196135 A * | 6/2023 | ............. A61C 19/06 |
| DE | 102004039937 A1 * | 2/2006 | ............. A01K 29/00 |

* cited by examiner

*Primary Examiner* — Heidi M Eide
(74) *Attorney, Agent, or Firm* — Nadya Reingand

(57) ABSTRACT

A method for installing ceramic veneers is proposed, which includes the steps of isolating the surface of a tooth from an oral cavity and preparing the tooth surface by sandblasting with an $Al_2O_3$ oxide powder. Next, the tooth surface is etched with orthophosphoric acid for 15-30 seconds, washed and dried, whereupon an adhesive layer is uniformly applied to the tooth surface and cured for 15-20 seconds. Further, a bonding agent layer equal in thickness to the adhesive layer is uniformly applied. Separately, the inner surface of a veneer is prepared by etching it with hydrofluoric acid for one minute and treating it with a ceramic primer, whereupon a bonding agent layer is uniformly applied to the veneer surface, and then a fixing composite layer is uniformly applied to the veneer surface. The veneer is installed on the tooth surface and light-curing is simultaneously performed with respect to all the layers.

5 Claims, No Drawings

METHOD FOR INSTALLING CERAMIC VENEERS WITHOUT TOOTH-GRINDING

CROSS-REFERENCE TO RELATED APPLICATIONS

This patent application is a Continuation in part of the U.S. application Ser. No. 17/617,933 which is a National stage application from PCT application PCT/RU2021/000049 filed Feb. 5, 2021.

TECHNICAL FIELD

The invention relates to the field of medicine, namely dentistry, and can be used for restoration of teeth without their grinding.

BACKGROUND OF THE INVENTION

U.S. Pat. No. 4,632,660 A (published 30 Dec. 1986) discloses a method for installing ceramic veneers without tooth-grinding, which comprises: preparing a surface of at least one veneer, preparing a surface of at least one tooth, and bonding them together using a light-curing adhesive cement. Said preparing the surface of the veneer includes immersing it in a bath of 12% hydrofluoric acid for etching for 12-15 minutes. Said preparing the surface of the tooth includes its etching with phosphoric acid of 30-40% concentration. The above method requires a long soaking of veneers in hydrofluoric acid and does not provide sufficient strength of fixation of the veneers, as the surface of the tooth is prepared only with phosphoric acid.

SUMMARY OF THE INVENTION

The objective of the present invention is to eliminate the disadvantages of the prior art. The technical result is to increase the strength of fixation of ceramic veneers without tooth-grinding.

The technical result is achieved by a method for installing ceramic veneers, which comprises the steps of isolating a surface of at least one tooth from an oral cavity and preparing the surface of the at least one isolated tooth by sandblasting with an $Al_2O_3$ oxide powder. Said sandblasting is carried out until the surface of the at least one isolated tooth becomes uniformly rough, after which the rough surface of the at least one isolated tooth is etched with orthophosphoric acid for 15-30 seconds. Then, the surface of the at least one isolated tooth is washed and dried, and an adhesive layer is uniformly applied to the surface of the at least one isolated tooth and cured for 15-20 seconds. After that, a bonding agent layer equal in thickness to the adhesive layer is uniformly applied, wherein an inner surface of at least one veneer is separately prepared by etching it with hydrofluoric acid for one minute. Further, the surface of the at least one the veneer is treated with a ceramic primer, a bonding agent layer is uniformly applied to the inner surface of the at least one veneer, and a fixing composite layer is uniformly applied to the surface of the at least one veneer. Next, the method proceeds to a final step, in which the veneer is installed on the surface of the tooth and light-curing is simultaneously performed with respect to: the adhesive layer on the surface of the tooth, the bonding agent layer on the surface of the tooth, the bonding agent layer and the fixing composite layer on the surface of the veneer.

The presence of the rough surface during the treatment of the at least one tooth is assessed using an optical magnifying device having a magnification of at least 5×.

When forming the rough surface, the condition is taken into account under which the surface of the at least one tooth should have an average surface roughness value ranging from 0.3 to 2 μm, which is assessed by laser scanning.

Ultra-thin veneers are used as the at least one veneer.

9.5% hydrofluoric acid is used.

The thickness of the bonding agent layer that is applied to the surface of the veneer is equal to the thickness of the bonding agent layer applied to the surface of the tooth.

Until the veneer is installed on the tooth and light-cured, the adhesive layer and the bonding agent layers which are applied to the at least one tooth, as well as the bonding agent layer and the fixing composite layer which are applied to the at least one veneer are all protected from intense forced and natural light radiation to eliminate a pre-polymerization process.

The thickness of the fixing composite layer applied to the veneer is equal to the thickness of the bonding agent layer applied to the surface of the veneer.

It should be noted that the aluminum oxide ($Al_2O_3$) powder having a particle size of 27 μm is used for said sandblasting. During said sandblasting, depending on the condition of the tooth being treated, an exposure time and a particle flow pressure are selected so that the roughness of the tooth being treated is more than 0.3 μm, and more preferably lies within 0.3-2 μm. The uniform surface roughness ensures good adhesion when using a multi-component adhesive system to attach the veneer to the tooth.

To prepare the surface of the veneer, 9.5% hydrofluoric acid is used.

To prepare the surface of the tooth, 37% orthophosphoric acid is used.

Said light curing is performed with a polymerization lamp having a maximum luminous flux power of at least 500 mW/cm².

As noted above, the surface of the at least one tooth is prepared by isolating it from the oral cavity using a cofferdam.

The above-indicated technical result is achieved by implementing the above-mentioned steps of the method in the specified order for treating the surfaces of veneers and teeth.

DETAILED DESCRIPTION OF THE INVENTION

A method for installing ceramic veneers without tooth-grinding comprises preparing the surface of at least one tooth, which involves initially isolating the at least one tooth (to be treated) from the rest of an oral cavity using a cofferdam and sandblasting the surface of the tooth with an aluminum oxide ($Al_2O_3$) powder typically having particles of about 27 μm in size. This size is optimal, since a larger particle size causes damage to the surface of the tooth. It should be noted that the surface of the tooth is sandblasted to obtain a uniform rough surface, which is an important factor for reliable adhesion of the surfaces of the tooth and the veneer when using a multi-component adhesive system. If there are areas with an unaffected tooth enamel on the treated surface of the tooth, the treatment should be continued. The presence of such untreated areas on the surface of the tooth leads to the formation of zones with poor adhesive properties. This can subsequently lead to the veneer peeling off from the tooth when exposed to natural factors. To effectively assess a degree of surface readiness, an optical magnifying device having a magnification of at least 5× is used, which makes it possible to visually assess the presence of the uniform rough surface.

To ensure more effective quality control of the prepared surface of the at least one tooth, a laser scanning technique is used. In this technique, the degree of surface roughness of the at least one tooth is assessed, which should have an average surface roughness value ranging from 0.3 to 2 µm.

The next step is to etch the surface of the tooth for 15-30 seconds with orthophosphoric acid, such as "Total Etch" (Ivoclar Vivadent), preferably having a 37% concentration, completely wash off the acid with distilled water, as a rule, for the same time as the etching itself, and dry the surface. Further, the multi-component adhesive system is used, which involves applying an adhesive and a separate bonding agent to the surface of the tooth. Thus, a uniform adhesive layer, for example, "Syntac Adhesive", is applied to the surface of the at least one isolated tooth and cured for 15-20 seconds. The bonding agent, such as Heliobond (Ivoclar Vivadent), is then applied to the surface in a thin layer. Light-curing adhesive and bonding agent are preferably used.

The method further comprises separately preparing the inner surface of at least one veneer by etching it for one minute with hydrofluoric acid, for example, "Porcelain Etchant" (Bisco). The use of hydrofluoric acid of 9.5% concentration is the best option for said one-minute etching. Next, the surface of the veneer is treated for one minute with a ceramic primer—silane, for example, "Monobond N". After that, a bonding agent, such as "Heliobond" (Ivoclar Vivadent), is evenly applied to the inner surface of the at least one veneer in a thin layer. If the bonding agent is applied to the surface in excess, it is subjected to air-blowing until a thin layer is formed. A fixing composite layer is then applied evenly on top of the bonding agent layer.

Preferably, the thickness of the bonding agent layer applied to the surface of the veneer is equal to the thickness of the bonding agent layer applied to the surface of the tooth. In this case, during polymerization, the layers give the same surface shrinkage, which eliminates the occurrence of tensile forces and stress concentration zones that can negatively affect the bonding strength of the ceramic veneers. The thickness of the fixing composite layer applied to the veneer (or to the tooth) should be selected similarly. Thus, the thickness of the fixing composite layer is preferably selected equal to the thickness of the bonding agent layer that is applied to the surface of the veneer.

The last step of the method is to bond the surface of the at least one veneer to the surface of the at least one tooth using a light-curing fixing composite, for example, using "Variolink Esthetic LC", which is applied to the surface of the veneer. However, the fixing composite can also be applied to the surface of the tooth. After the veneer is installed on the tooth, the following are simultaneously cured: the adhesive layer on the surface of the tooth, the bonding agent layer on the surface of the tooth, the bonding agent layer and the fixing composite layer on the surface of the veneer. To achieve the technical result aimed at increasing the bonding strength of the ceramic veneers without tooth-grinding, it is also important to carry out the curing step of all the layers (i.e., the adhesive layer on the surface of the tooth, the bonding agent layer on the surface of the tooth, the bonding agent layer on the surface of the veneer, the fixing composite layer) only after installing the veneer on the tooth. This feature of the proposed method eliminates inaccuracies in installing the veneer (distortions, voids, poor adhesion), which allows installing the veneer exactly in the position in which the control fitting was carried out. In this case, maximum adhesion of the surfaces of the tooth and the veneer will be ensured. Preferably, prior to the installation of the veneer on the tooth and the light-curing process, the adhesive and bonding agent layers applied to the at least one tooth, as well as the bonding agent and fixing composite layers applied to at least one veneer are protected from intense forced and natural light radiation to avoid a pre-polymerization process.

All the layers can be illuminated with a polymerization lamp having a luminous flux power of at least 500 mW/cm$^2$ for about two to five seconds. The excess material is removed, and a final illumination is carried out for approximately 10 seconds each on the veneer side and on the tooth side (back side).

Due to the presence of the several layers that are cured simultaneously, a high intensity of light exposure may cause a sharp increase in stress in the layers due to the onset of an abrupt polymerization process. Therefore, it is preferable to apply a gradual increase in the intensity of light exposure to the layers (i.e., the adhesive layer on the surface of the tooth, the bonding agent layer on the surface of the tooth, the bonding agent layer on the surface of the veneer, the fixing composite layer on the surface of the veneer), starting with a luminous flux power of 100 mW/cm$^2$ and bringing to the luminous flux power to 500 mW/cm$^2$ by gradually increasing it over a period of 2-10 seconds. That is, it is preferable to use a polymerization lamp which has a function of gradually adjusting the luminous flux power from 100 mW/cm$^2$ to 500 mW/cm$^2$.

The combination of the above-described steps with the use of the appropriate substances allows for a higher bonding strength of the ceramic veneer to the tooth without having to grind the tooth.

The invention uses veneers made in a dental laboratory after the following steps.

Two impressions of the upper and lower jaws are taken, the bite is registered, and readings of the facial arch are taken. The information is transferred to the laboratory to make a plaster model of the teeth. A wax model of the required number of teeth is made by applying wax to the front surface of the plaster model of the teeth to obtain a new mold. The mold is tried on top of the teeth. The mold is evaluated by length and color and approved with a patient. Retraction is performed and two silicone impressions are taken using a sandwich technique, the bite is re-registered. Then, the obtained information is transferred to the laboratory to make at least one veneer. It is worth noting that the specified time intervals are not absolutely strict to comply with. Of course, small errors in the execution of the steps are allowed—for example, an error of about 1 second is allowed for said 15-30-second etching with orthophosphoric acid and said 15-20-second treatment with adhesive. And for said one-minute etching with hydrofluoric acid and said one-minute treatment with the ceramic primer, an error of 1-2 seconds is allowed.

The proposed solution has been tested many times. All the stated requirements have been confirmed.

Thus, the use of the proposed invention allows to increase the strength of fixation of ceramic veneers without tooth-grinding.

The inventio claimed is:
1. A method for installing ceramic veneers, comprising:
   isolating a surface of at least one tooth from an oral cavity; and
   preparing the surface of the at least one tooth by:

sandblasting the surface of the at least one tooth with an Al$_2$O$_3$ oxide powder until the surface of the at least one tooth becomes uniformly rough;

after said sandblasting, etching the surface of the at least one tooth with orthophosphoric acid for 15-30 seconds;

washing and drying the surface of the at least one tooth;

uniformly applying an adhesive layer to the surface of the at least one tooth and curing the adhesive layer for 15-20 seconds;

then uniformly applying a bonding agent layer equal in thickness to the adhesive layer;

wherein the method further comprises separately preparing an inner surface of at least one veneer by:

etching the inner surface of the at least one veneer with hydrofluoric acid for one minute;

treating the inner surface of the at least one the veneer with a ceramic primer;

uniformly applying a bonding agent layer to the inner surface of the at least one veneer; and uniformly applying a fixing composite layer to the inner surface of the at least one veneer;

wherein the at least one veneer is installed on the surface of the at least one tooth, while simultaneously performing light-curing with respect to: the adhesive layer on the surface of the at least one tooth, the bonding agent layer on the surface of the at least one tooth, the bonding agent layer and the fixing composite layer on the inner surface of the at least one veneer, wherein the light-curing begins with a luminous flux power of 100 mW/cm$^2$ and is brought up to a luminous flux power of 500 mW/cm$^2$ by gradually increasing it over a period of 2-10 seconds;

wherein a thickness of the bonding agent layer applied to the inner surface of the at least one veneer is equal to a thickness of the bonding agent layer applied to the surface of the at least one tooth;

and wherein a thickness of the fixing composite layer applied to the inner surface of the at least one veneer is equal to a thickness of the bonding agent layer applied to the inner surface of the at least one veneer;

and wherein until the at least one veneer is installed on the at least one tooth and said light-curing is performed, the adhesive layer and the bonding agent layer which are applied to the surface of the at least one tooth, as well as the bonding agent layer and the fixing composite layer which are applied to the inner surface of the at least one veneer are protected from intense forced and natural light radiation to avoid a pre-polymerization process.

2. The method of claim 1, wherein an optical magnifying device having a magnification of at least 5× is used, during said sandblasting, to determine that the surface of the at least one tooth becomes uniformly rough.

3. The method of claim 1, wherein said sandblasting is performed until the surface of the at least one tooth has an average surface roughness value ranging from 0.3 to 2 μm, which is assessed by laser scanning.

4. The method of claim 1, wherein the at least one veneer is an ultra-thin veneer.

5. The method of claim 1, wherein the hydrofluoric acid is 9.5% hydrofluoric acid.

* * * * *